United States Patent [19]

Kiel et al.

[11] Patent Number: 5,003,050
[45] Date of Patent: Mar. 26, 1991

[54] DIAZOLUMINOMELANIN AND A METHOD FOR PREPARING SAME

[75] Inventors: Johnathan L. Kiel; Gerald J. O'Brien, both of San Antonio, both of Tex.

[73] Assignee: The United States of America as represented by the Secretary of the Air Force, Washington, D.C.

[21] Appl. No.: 489,561

[22] Filed: Mar. 7, 1990

[51] Int. Cl.$^5$ .................... C07C 245/00; C09B 39/00; A61B 5/00
[52] U.S. Cl. .................................. 534/573; 424/1.1; 424/9; 435/7.2; 435/7.5; 435/7.8; 435/968; 436/164; 436/172; 436/501; 436/514; 436/518; 436/805; 514/150; 524/198; 534/769; 534/767; 534/789; 534/790
[58] Field of Search .................... 534/769, 573 P, 790, 534/767, 789

[56] References Cited

U.S. PATENT DOCUMENTS

| | | | |
|---|---|---|---|
| 4,619,990 | 10/1986 | Elmasry et al. | 534/573 |
| 4,743,541 | 5/1988 | Higgins et al. | 435/7 |
| 4,745,077 | 5/1988 | Holian et al. | 436/526 |
| 4,748,116 | 5/1988 | Simonsson et al. | 435/23 |
| 4,765,961 | 8/1988 | Schiff et al. | 422/52 |
| 4,766,150 | 8/1988 | Kiel | 514/567 |
| 4,788,142 | 11/1988 | Hosaka et al. | 435/29 |

FOREIGN PATENT DOCUMENTS

| | | | |
|---|---|---|---|
| 58-63775 | 4/1983 | Japan | 534/573 P |
| 1240774 | 6/1986 | U.S.S.R. | 534/789 |
| 811953 | 4/1959 | United Kingdom | 534/789 |

OTHER PUBLICATIONS

Drain et al, Chemical Abstracts, vol. 83, #10878v (1975).

Savin et al, Chemical Abstracts, vol. 68, #69638k (1968).

Primary Examiner—Floyd D. Higel
Attorney, Agent, or Firm—Charles E. Bricker; Donald J. Singer

[57] ABSTRACT

A water-soluble luminescent compound having repeating units of the formula:

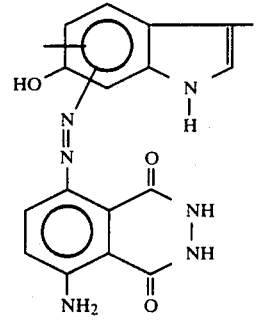

The product, which is a polymer having repeating units comprising diazo-linked luminol and hydroxyindole, is referred to as diazoluminomelanin (DALM), since one of the precursors to this product, 3-amino-L-tyrosine (3AT) is closely related to the biological substrates which are converted into melanin.

Also provided is a method for preparing DALM which comprises reacting 3AT with an alkali metal nitrite, and reacting the resulting diazonium salt with luminol.

DALM can be used for chemiluminescent immunoassays for biological and chemical agents; in radiofrequency and ionizing radiation dosimeters; and for RNA/DNA hybridization assays for viruses and genetic detection.

12 Claims, 4 Drawing Sheets

DIAZOLUMINOMELANIN AND A METHOD FOR PREPARING SAME

RIGHTS OF THE GOVERNMENT

The invention described herein may be manufactured and used by or for the Government of the United States for all governmental purposes without the payment of any royalty.

BACKGROUND OF THE INVENTION

This invention relates to luminescent reagents.

Specific binding assays provide an economical means for detecting and measuring an analyte present in low concentrations in a sample. Specific binding assays are based upon the interaction of two bindable substances, one the analyte and the other a specific binding partner, which specifically recognize each other. Examples of specific binding partners whose interaction can serve as the basis for a specific binding assay include antigens-antibodies, biotin-avidin, nucleic acid probes, enzymes-substrates, enzymes-inhibitors, enzymes-cofactors, chelators-chelates, and cell surface receptor pairs. Assays involving other specifically bindable substances are also known and within the scope of the present invention. Specific binding assays have shown great utility in determining various analytes in biological, medical, environmental, agriculture and industrial applications.

A variety of assays using the principles of the specific binding approach are known, and several have become important diagnostic tools. In one such type of specific binding assay, the immunoassay, the analyte is an antibody, antigen, or hapten, and is made to react with another member of this group. While the background discussion will focus on such immunoassays, this focus is made for clarity of presentation, and is not to be interpreted as limiting of the invention.

A variety of labelling reactions have been proposed for use in specific binding assays, including radioactive, enzymatic, chromogenic and luminogenic procedures. In a radioactive labelling procedure, the component conjugated with the specific binding partner is an atom or molecule which emits radioactivity. Chromogenic and luminogenic labelling reactions are chemically more complex, in that several reactants may be involved. The chromophore or lumiphore may itself be the label in the reaction, or a catalyst, typically an enzyme, may be used as the label. When the catalyst is used as the label, it will react with catalytic substrates which in turn produce color or luminescence. The remaining components of the reaction, that is, those not conjugated to the binding partner, are supplied in a chromogenic or luminogenic reagent medium, so that the uniting of the labelled conjugate and the reagent medium results in the desired color change or light emission, respectively.

Luminescent labels are attractive alternatives for use in specific binding assays for a variety of reasons. Luminescence is broadly defined as the production of visible light by atoms that have been excited by the energy produced in a chemical reaction, usually without an associated production of heat. Chemical energy excites electrons in the light-emitting molecules to higher energy states, from which electrons eventually fall to lower energy states with the emission of quanta of energy in the form of visible light. Luminescence is observed in several synthetic chemical compounds and also in naturally occurring biological compounds such as found in fireflies and certain varieties of fish.

One of the most important families of chemiluminescent molecules are the phthalylhydrazides. The most familiar member of this family is luminol, or 5-amino-2,3-dihydro-1,4-phthalazinedione, which has a gross chemical composition of $C_8H_7N_3O_2$ and a double ring structure with a melting point of about 320° C. Luminol is commercially available from several suppliers and is well characterized. Certain luminol analogs are also chemiluminescent, such as those wherein the position of the amino group is shifted (e.g., isoluminol, the amino group being at the 6 position), or is replaced by other substituents, as well as annelated derivatives and those with substitution in the nonheterocyclic ring. Some luminol analogs produce light more efficiently than does luminol itself, while others have lower efficiency. (As used herein, the term "luminol" encompasses such related species.)

Generally, luminol produces light in an oxidizing reaction, wherein the luminol combines with oxygen or an oxidizer to produce a reaction product and photons at a wavelength of about 425–450 nanometers (nm). The precise reaction formula and the quantum efficiency of light production, i.e., the ratio of luminescing molecules to total molecules of the luminescent species, depend upon the medium in which the luminol resides, temperature and other reaction conditions. Typical oxidizers used in conjunction with luminol include oxygen, hydrogen peroxide, hypochlorite, iodine and permanganate.

The oxidation of luminol with the associated production of light occurs rather slowly at ambient temperatures, unless the reaction is catalyzed. A variety of different substances can catalyze the reaction, including organic enzymes, e.g., horseradish peroxidase, other organic molecules such as microperoxidase and heme, positive metallic ions such as the cupric ion, and negative ions such as the ferricyanate ion.

Luminescent molecules would appear to be highly desirable as tags in specific binding assays because of their stability, sensitivity, the potential ease of detecting their emitted visible light and their lack of toxicity. Commercial luminol, however, has proven to be unsuitable for such purposes. There exists a need for specific improvements in the light emission characteristics of the reaction for use with such assays. Heretofore, commercial luminol has not shown sufficient activity to be useful to measure analytes at low concentrations in specific binding assays. The light emission intensity of the luminol reaction may be sufficient where high concentrations of catalyst are employed and where highly sophisticated and sensitive photometers are available, but the luminescent intensity has not been sufficient with low concentrations of catalyst and where other detection media such as photographic film or less sensitive photometers are used.

While the luminol reaction therefore offers important potential benefits in the measurement of the presence and amount of a reaction component, for many potential applications, the intensity of the emitted light is too low. Further, the light emitted from commercial luminol exhibits an early flash of light within the first few seconds of the initiation of the reaction, followed by a progressive and rapid decrease in light emission over time. The integrated light intensity during any fixed period of time is therefore likely to be different from that measured over any other equal period of time. This variability may result in irreproducibility between tests. Desirably, there would be some period of time during which the light emission from the luminol reaction is relatively constant, so that the measurement of integrated light intensity could begin at different times after initiation of the reaction, but within the period of constant light output, without variability of the results. This would eliminate the requirement that the reagents be added to a solution fixed in front of the luminescence detector which puts severe constraints on the light measuring system.

Higgins et al, U.S. Pat. No. 4,743,541, disclose that the intensity and duration of emitted light from luminol can be considerably improved by repeatedly dissolving and recrystallizing the luminol until sulphide and hydrazine levels are below about 100 ppm.

The production of chemiluminescence with luminol comprises dissolving the luminol in an organic solvent, such as DMSO or acetone, or in a strong base and diluting the solution in a buffer of desired pH. The amount of luminol that can be dissolved is severely limited by the relative insolubility of luminol in water at a pH below 10.

When luminol is covalently attached to carriers such as protein, its chemiluminescence is quenched. Isoluminol, although less efficient in light production than luminol, is quenched to a lesser degree by covalent attachment. The noncovalent attachment of luminol to bovine serum albumin prevents quenching and solubility problems, but "leaks" luminol into the solution by forming an equilibrium between bound and unbound luminol, thus decreasing the specificity of luminol/carrier dependent immunoassays and enzyme-linked assays.

There is a need for a luminescent probe which is water soluble, is highly quantum efficient, and provides long-lived chemiluminescence.

Accordingly, it is an object of the present invention to provide a water-soluble luminescent compound.

Other objects, aspects and advantages of the present invention will be apparent to those skilled in the art from a reading of the following detailed disclosure of the invention.

SUMMARY OF THE INVENTION

In accordance with the present invention there is provided a water-soluble luminescent compound having repeating units of the formula:

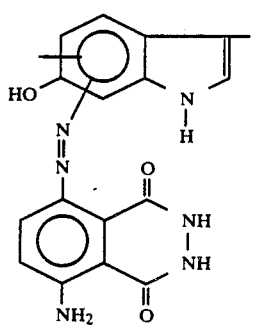

The product, which is a polymer having repeating units comprising diazo-linked luminol and hydroxyindole, is hereinafter referred to as diazoluminomelanin (DALM), since one of the precursors to this product, 3-amino-L-tyrosine (3AT) is closely related to the biological substrates which are converted into melanin.

Also provided in accordance with the invention is a method for preparing DALM which comprises reacting 3AT with an alkali metal nitrite, and reacting the resulting diazonium salt with luminol.

DETAILED DESCRIPTION OF THE INVENTION

Figure 1:
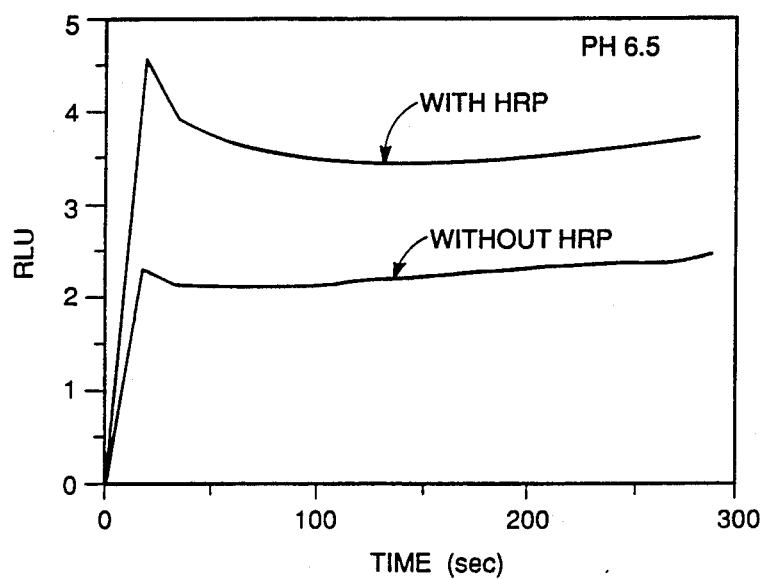
FIGS. 1-3 illustrate the chemiluminescent response of DALM at pH 6.5, 7.4 and 9.5, respectively.

DALM is prepared by reacting 3AT with an alkali metal nitrite, such as sodium nitrite, and thereafter reacting the resulting diazotized product with luminol. At some point in the reaction, the alaninyl portion of the 3AT rearranges to provide the hydroxyindole portion of the final product. It is believed that such rearrangement occurs following coupling of the luminol to the diazotized 3AT.

The reaction between 3AT and the alkali metal nitrite is carried out in aqueous medium. Since diazotization reactions are, in general, exothermic, it is presently preferred to carry out this reaction under isothermal conditions or at a reduced temperature, such as, for example, at ice bath temperatures. The reaction time for the diazotization can range from about 1 to 20 minutes, preferably about 5 to 10 minutes.

Because of the relative insolubility of luminol in aqueous medium, the luminol is dissolved in an aprotic solvent, such as dimethylsulfoxide (DMSO), then added, with stirring, to the aqueous solution of diazotized 3AT. This reaction is carried out, at reduced temperature, for about 20 to 200 minutes. The solvent is then removed by evaporation at low pressure, with moderate heating, e.g., about 30° to 37° C.

The reaction mixture is acidic, having a pH of about 3.5. The coupling of the luminol and the diazotized 3AT can be facilitated by adjusting the pH of the reaction mixture to about 5.0 to 6.0.

The product DALM may be precipitated from the reaction mixture by combining the reaction mixture with an excess of a material which is not a solvent for the DALM, e.g., acetone. After centrifuging the precipitate and discarding the supernatant, the solid material may be dried under vacuum.

In general, the quantities of the 3AT, alkali metal nitrite and luminol reactants are equimolar. It is, however, within the scope of the invention to vary the quantities of the reactants. The molar ratio of 3AT:luminol may be varied over the range of about 0.6:1 to 3:1.

DALM is water soluble, having an apparent pKa for solubility about pH 5.0. DALM does not require a catalyst for chemiluminescence. The duration of the reaction is in excess of 52 hours. In contrast, luminol requires a catalyst; with micro peroxidase as the catalyst, luminol has shown peak luminescence at 1 sec and half-lives of light emission of 0.5 and 4.5 sec at pH 8.6 and 12.6, respectively. The chemiluminescence yield of DALM is better at pH 7.4 than at pH 9.5, although it still provides a strong signal at strongly basic pHs. DALM also produces chemiluminescence at pH 6.5 which is about the same intensity as that produced at pH 9.5.

DALM can be used for chemiluminescent immunoassays for biological and chemical agents; in radiofrequency and ionizing radiation dosimeters; and for RNA/DNA hybridization assays for viruses and genetic detection.

The following examples illustrate the invention. In the examples, luminol, 3-amino-L-tyrosine hydrochloride (3AT), horseradish peroxidase (donor:hydrogen peroxide oxidoreductase; E.C. 1.11.1.7) type VI, dimethyl sulfoxide (DMSO), phosphate buffer salts, and gel filtration and ion exchange materials were obtained from Sigma Chemical Company, St. Louis, Mo. Other buffer salts were obtained from Fisher Scientific, Houston, Tex. 3% hydrogen peroxide was obtained from Hydrox Chemical Company, Elk Grove Village, Ill.

Luminometric measurements were made using a TD-20e luminometer (Turner Designs, Mountain View, Calif.). In most cases, the samples in the instrument were held at 37° C. in an aluminum block by circulating water from a thermostatically controlled water bath.

Electron spin resonance (ESR) spectra were made using a Varian E-line spectrometer operating at 9.48 GHz, 10 mW power, and a field set of 3353 G. The scan range was 400 G, with a modulation amplitude of 16 G, a time constant of 3 sec, a receiver gain of $2 \times 10^3$, a modulation frequency of 100 KHz and a scan time of 2 min.

Chemiluminescence in the radiofrequency radiation field (2450 MHz, 25 W, continuous wave) was measured using the Quantitative Luminescence Imaging System (QLIS) described in U.S. patent application Ser. No. 241,992, filed Sept. 8, 1988, now U.S. Pat. No. 4,948,975. Briefly, the QLIS is constructed from a coherent fiber optic image guide contained in a circularly polarized (wire mesh) microwave guide powered by a RF power generator, a video camera and an image processor. The QLIS was calibrated using a solid-state scintillator with phosphor #5000 (520-nm emission peak) and a carbon-14 activator of 17.5 mCi. The calibration source was held in an adaptor which allowed the source to be coupled to the input window of the fiber optic bundle. Chemiluminescent solutions were held in 1.0×1.0×4.5 cm polyacrylate cuvettes which were, in turn, held in a polyacrylate holder which connected to the fiber optic bundle input face of the QLIS. Temperature was measured during microwave radiation in the center of the solution in each cuvette with a nonperturbing electrothermia probe and monitor.

Chemiluminescent emission spectra were measured in a Photo Research PR-713 Spectro Radiometer. Fluorescent spectra were measured in an Aminco-Bowman Spectrophotofluorometer. Colorimetric measurements were made using a Bausch and Lomb Spectronic 2000 spectrophotometer (500 nm wavelength light, polystyrene cuvettes).

EXAMPLE I

Preparation of DALM

DALM was prepared by combining 10 mM aqueous solutions of 3AT and sodium nitrite, and after a 5 min preincubation, adding a 10 mM solution of luminol in DMSO. After allowing the materials to react for 50 min. the reaction was stopped by adding an equal volume of acetone followed by the addition of a saturated NaOH solution (10% total volume of the reaction mixture). This mixture turned dark brown. After several days, crystals formed on the surface and bottom of the reaction mixture. These crystals were removed by filtration, washed with acetone and dried. Dried, acetone-precipitated DALM displayed an ESR spectrum indicating that it could form stable free radicals. The signal was still present in the sample two months later (only 20% diminished).

An alternate form of the above compound was prepared by carrying out the reaction in the presence of a magnetic fluid (magnetite) prepared from ferrous sulfate and ferric sulfate, in place of the water solution. The magnetic fluid was prepared by mixing 150 ml of 0.67M ferrous sulfate with 100 ml of 1.0M ferric sulfate. While mixing the fluid, 128 ml of 250 g/l NaOH was added. The pH was adjusted to 11 to 12 by adding more NaOH solution at 35° C. The material was continuously mixed for 20 min. 60 ml of 15% sodium oleate was then added to the mixture. Upon cooling, the pH was adjusted to 5.5 with 1N HCl. The magnetic particles were washed and the wash water decanted 10 times. The particles were then filtered and dried. The magnetic powder was resuspended in a 1% aqueous solution of sodium dodecylbenzene to make the magnetic fluid. Yet another alternate form was prepared by adding manganese chloride (5 mM) to some of the sodium salt.

The chemiluminescent and fluorescent emission peaks of 3AT, luminol and DALM are shown in Table I, below.

TABLE I

Peak Wavelengths (nm) of Excitation and Chemiluminescent/Fluorescent Emissions

| Compound | Excitation | Emission Chemiluminescence | Fluorescence |
|---|---|---|---|
| 3AT | 256 | — | 365 |
|  | 360 | — | 420 |
| Luminol | 275 | — | 425 (water) |
|  | — | — | 510 (DMSO) |
|  | — | 425 (water) | — |
|  |  | 510 (DMSO) | — |
|  |  | 484 (water/DMSO) | — |
| DALM | 365 | — | 480 |
|  | — | 519 (major peak) | — |
|  |  | 600 (minor peak) | — |

Examination of the above table reveals that the chemiluminescence and fluorescence of luminol are at the same wavelength, both being shifted alike depending on the solvent used. In contrast, the emissions for DALM are distinctly different.

Solutions of 10 mM luminol in DMSO, 10 mM 3AT in water and 100 mM sodium nitrite in water were prepared. These solutions were mixed in various proportions, with the DMSO/water ratio constant to determine the optimum reactant ratio. Table II, below, illustrates the effect of varying the 3AT/luminol molar ratio with 3AT+luminol at 10 mM and sodium nitrite at

TABLE II

| Reactant Ratio vs Absorbance | |
|---|---|
| 3AT/luminol molar ratio | Colorimetric absorbance at 500 nm |
| 0.15 | 0.0 |
| 0.35 | 0.028 |
| 0.6 | 0.108 |
| 1.0 | 0.234 |

TABLE II-continued

| 3AT/luminol molar ratio | Colorimetric absorbance at 500 nm |
|---|---|
| 1.65 | 0.29 |
| 3.0 | 0.236 |
| 7.0 | 0.15 |

EXAMPLE II

Chemiluminescent Response of DALM

Figure 2:
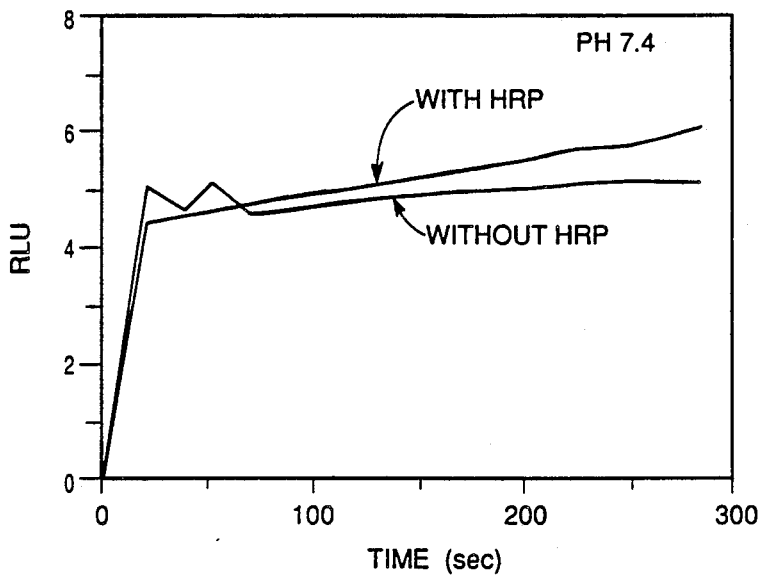
Figure 3:
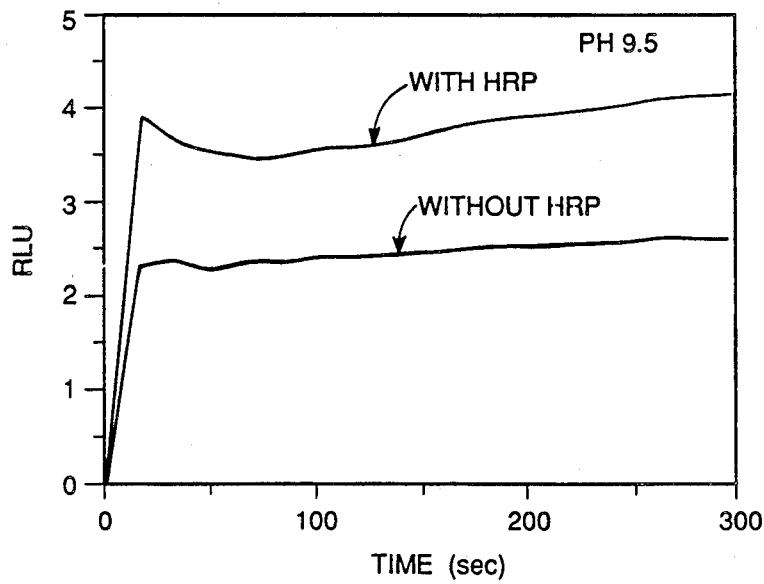

The chemiluminescent response of DALM at 10 microgram/ml at pH 6.5, 7.4 and 9.5, with and without horseradish peroxidase (22.5 mM HRP) at 37° C. is shown in FIGS. 1-3, respectively. The reactions were initiated by adding 100 microliters of 8.8 mM hydrogen peroxide to 900 microliters 0.1M phosphate (pH 6.5 or 7.4) or Tris HCl (pH 9.5) buffer containing DALM or DALM and HRP. Counts were for 10 sec out of every 16 sec using a Turner Designs 20e luminometer.

Referring to FIGS. 1-3, it can be seen that the output of light increased or was near steady-state over about 5 minutes of reaction time (at 37° C.) for pH 6.5, 7.4 and 9.5. These figures also show that HRP at 22.5 mM no more than doubled the chemiluminescence. The reaction ran without the presence of peroxidase, and equally well at pH 6.5 and 9.5. It can also be seen that of the three pH's examined, pH 7.4 provided the best results.

EXAMPLE III

Microwave Radiation Exposure

Reaction mixtures for microwave radiation exposure were prepared by combining 0.75 ml of 1M sodium carbonate containing 1 mg/ml luminol and 0.75 ml DALM solution (1 mg/ml, Na salt). The reaction mixtures were placed in polyacrylate cuvettes in the QLIS (described previously). 100 µl 3% hydrogen peroxide was added to each reaction mixture. The resulting mixture was activated with microwave radiation at 2450 MHz, continuous wave, 25 W input power.

Figure 4:
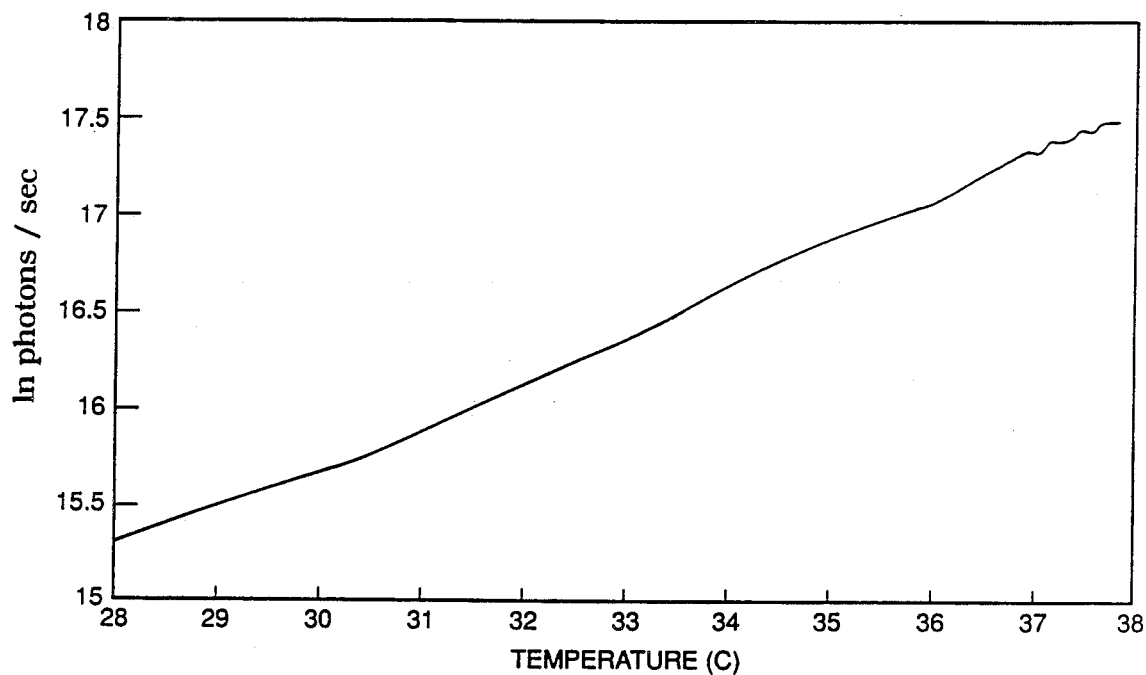
FIG. 4 illustrates the thermochemiluminescent response of a DALM/luminol solution.

Referring to FIG. 4, it can be seen that the activated solution produced light proportional to the temperature. The emission reaction established long-term steady-states for temperatures between 25° and 60° C. (The range from 28° to 38° C. is shown in FIG. 4) The temperature (Celsius) vs l n of lumin escence plot was linear with a correlation coefficient of 0.998. The activation energy for the reaction is 43 kcal/mole (180 kjoules/mole). Temperature $T_n$ can be determined from emission data by the formula:

$$T_n = \{(\ln Q_n - \ln Q_0)/0.2335077\} + T_0$$

where $Q_0$=photons/sec emission at starting temperature $T_0$, and $Q_n$=photons/sec emission at final temperature $T_n$. The instantaneous specific absorption rate of (thermal) energy ($P_I$) can be approximated by the formula:

$$P_I = Q_T/Q_E$$

where $Q_E$=photons per joule of energy input and $Q_T$=photons/sec emission at a given temperature. The difference between the instantaneous specific absorption rate with and without irradiation divided by the pulse width of the radiation gives the microwave power absorption rate per pulse. $Q_E$ is determined from the absolute quantum yield of the luminescent fluid (approximately $7.5 \times 10^{21}$ photons/mole for luminol) divided by the activation energy ($1.8 \times 10^5$ joules/mole).

EXAMPLE IV

DALM as a Microwave Radiation Absorber

Figure 5:
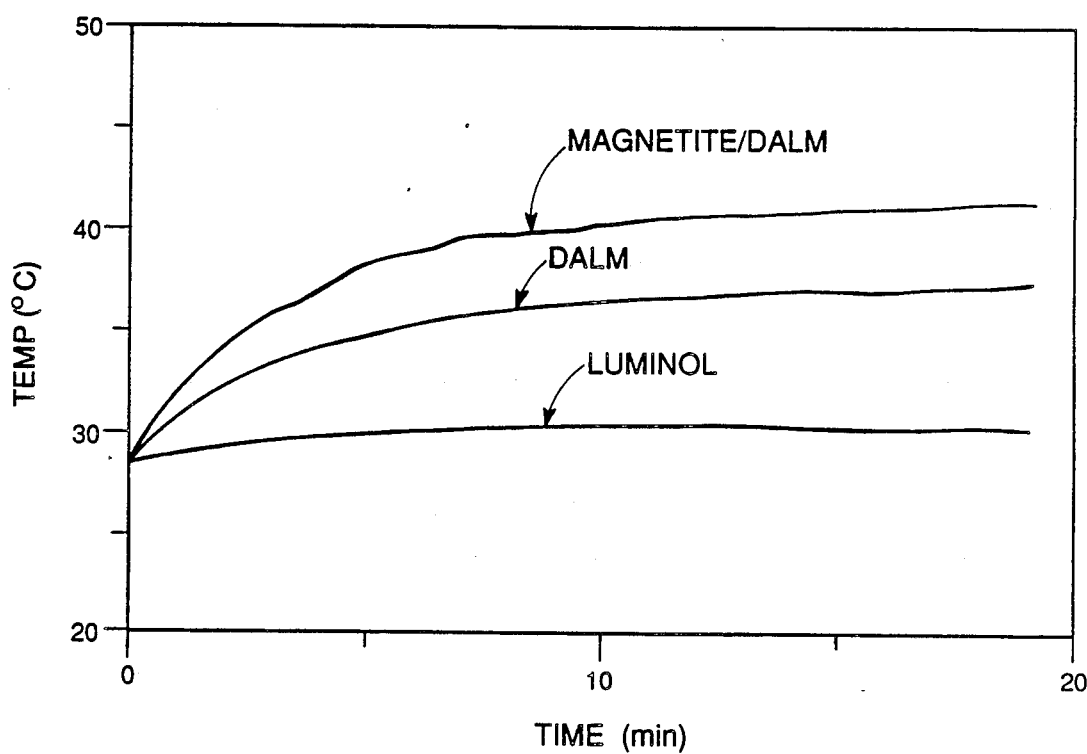
FIG. 5 illustrates the absorption of microwave radiation by DALM.

Solutions of (A) luminol (1 mg/ml) in 1M sodium carbonate, (B) DALM (Na salt, 500 µg/ml) and luminol (500 µg/ml) in 0.5M sodium carbonate, and (C) DALM (Na salt, 333 µg/ml), magnetite DALM (prepared as in Example I)(667 µg/ml) and luminol (333 µg/ml) in 0.33M sodium carbonate were activated with 100 µl 3% hydrogen peroxide, then exposed to microwave radiation at 2450 MHz, continuous wave, 25 W input power. FIG. 5 illustrates the enhanced absorption of microwave radiation by DALM and DALM/magnetite.

EXAMPLE V

Plasmid DNA/DALM Copolymer

20 µl 10 mM sodium nitrite and 20 µl 10 mM 3AT were added to 4 µg (20 µl 0.236 µg/ml) deoxyriboguanosine-tailed pBR322. The mixture was incubated for 2 min at room temperature (RT). 60 µl 10 mM luminol in DMSO was then added. The mixture was incubated for 30 min at RT.

Figure 6:
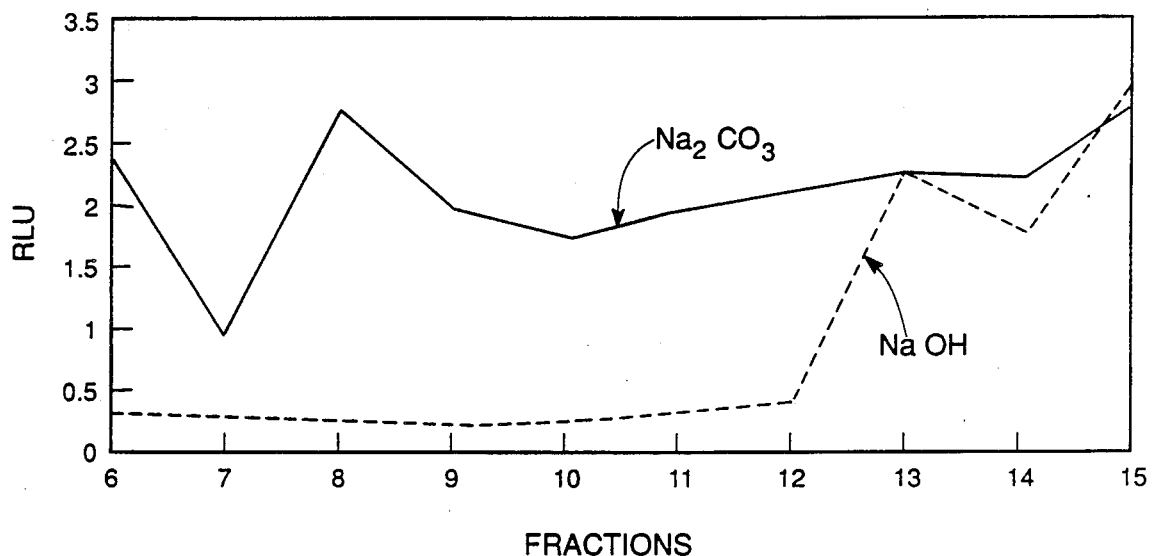
FIG. 6 illustrates the luminescent response of DNA/DALM copolymer (fractions 6-15)

The resulting copolymer was eluted through a G-50-150 Sephadex column equilibrated in SET buffer (50 mM Tris, pH 7.5); 1 mM ethylene diamine tetraacetate (EDTA); and 100 mM NaCl). 150 µl fractions were taken as the material eluted from the column. One microliter of each fraction was added to 300 µl of 3% hydrogen peroxide and 300 µl 1M sodium carbonate; one microliter of each fraction was added to 200 µl of SET buffer, 100 µl 1N sodium hydroxide, and 300 µl 3% hydrogen peroxide. Luminescence was recorded at 37° C. for 10 sec integration times for each sample. Referring to FIG. 6, fractions 7-10 contained the DNA based on 260 nm spectrophotometric peak absorbance of unlabeled DNA and electrophoresis and subsequent staining with ethidium bromide. The sodium carbonate technique revealed the DNA/DALM luminescence and the luminescence of free DALM components. The sodium hydroxide technique revealed only the free DALM component luminescence.

EXAMPLE VI

DALM as a Substrate for Green Hemoprotein (GHP)-mediated Peroxidation

Figure 7:
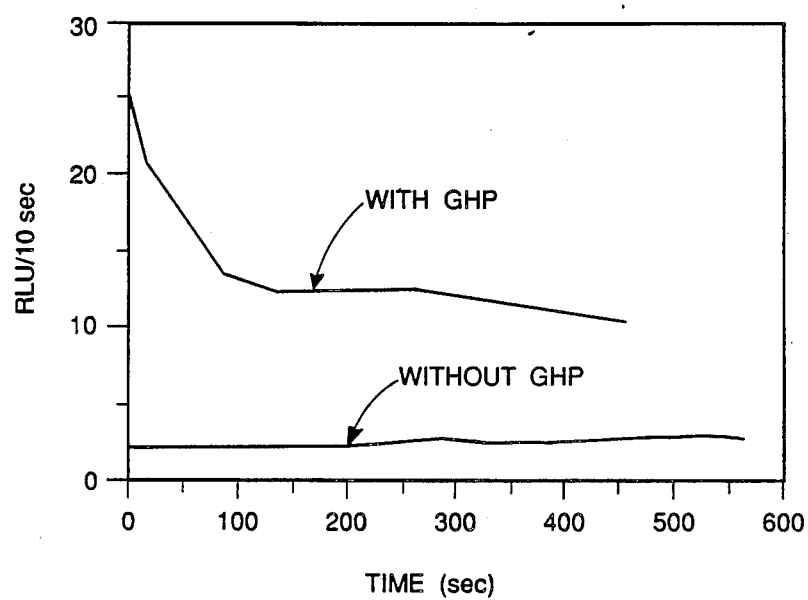
FIGS. 7-8 illustrate the luminescent response of DALM to green hemoprotein.

Green hemoprotein was obtained from fresh human hemolysate in partially purified form. 100 µl GHP solution with an optical absorbance of 0.2 at 416 nm was mixed with 37.5 µg DALM in 620 µl of 1 mM, pH 7.4, sodium phosphate buffer containing 0.0003% hydrogen peroxide. The luminescence of this reaction was monitored with the TD-20e Luminometer and compared to the reaction without GHP. Referring to FIG. 7, it can be seen that the GHP-containing solution yielded a 5- to 20-fold increase in luminescence compared to the baseline luminescence of uncatalyzed DALM peroxidation.

Figure 8:
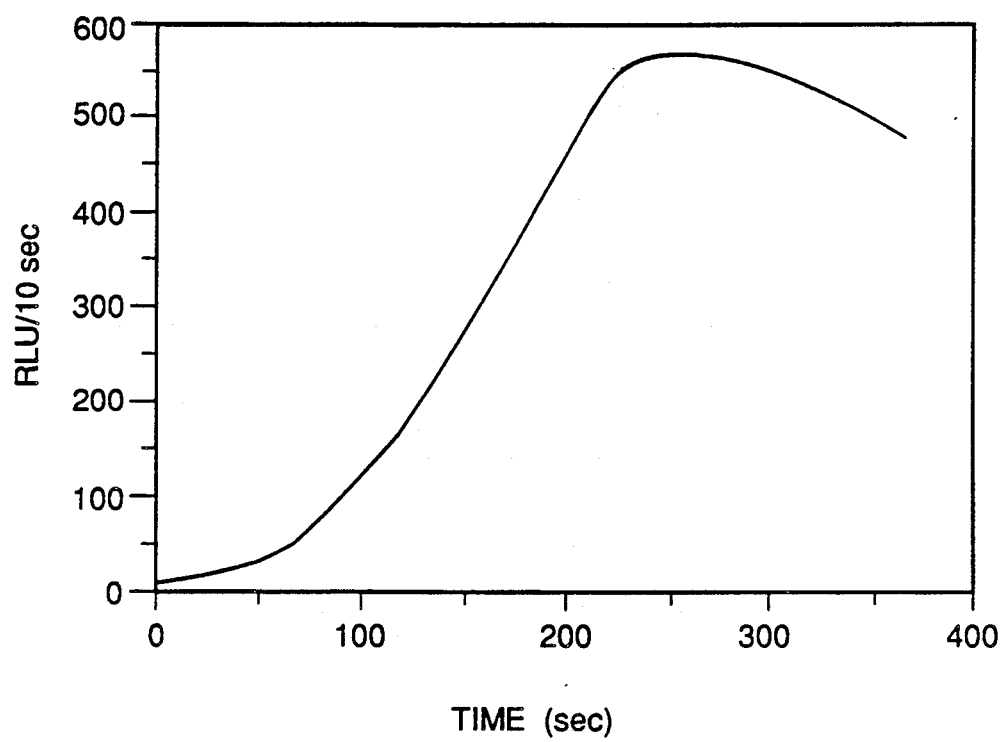

300 µl of 1 mM, pH 7.4, sodium phosphate buffer containing 10 µg/ml DALM was activated with 100 µl 0.001% hydrogen peroxide, followed by the addition of two 10 µl aliquots of GHP solution (0.10 O.D. at 412 nm and 0.27 O.D. at 414 nm, respectively) at 30 and 48 sec. Referring to FIG. 8, it can be seen that GHP increased the baseline chemiluminescence of DALM by over 500-fold with about 70 μM hydrogen peroxide.

Various modifications may be made to the invention as described without departing from the spirit of the invention or the scope of the appended claims.

We claim:

1. A luminescent compound having repeating units of the formula:

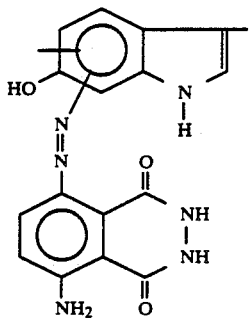

2. A method for preparing a luminescent compound having repeating units of the formula:

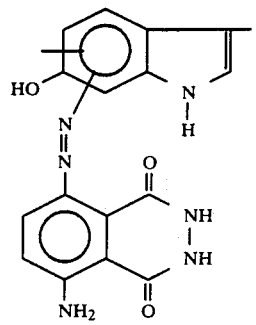

which comprises the steps of (a) reacting 3-amino-L-tyrosine with an alkali metal nitrite to form a diazonium salt, (b) reacting said salt with 5-amino-2,3-dihydro-1,4-phthalazinedione and (c) recovering the resulting compound.

3. The method of claim 2 wherein said reacting step (a) is carried out in aqueous solution.

4. The method of claim 3 wherein said aqueous solution is acidic.

5. The method of claim 4 wherein said aqueous solution has a pH of about 5.0 to 6.0.

6. The method of claim 2 wherein said reacting step (a) is carried out for about 1 to 20 minutes.

7. The method of claim 6 wherein said reacting step (a) is carried out for about 5 to 10 minutes.

8. The method of claim 2 wherein said reacting step (a) is carried out at a temperature of about 0° C. to room temperature.

9. The method of claim 2 wherein the amounts of said 3-amino-L-tyrosine and said alkali metal nitrite are approximately equimolar.

10. The method of claim 2 wherein said reacting step (b) is carried out for about 20 to 200 minutes.

11. The method of claim 2 wherein the molar ratio of 3-amino-L-tyrosine to 5-amino-2,3-dihydro-1,4-phthalazinedione is in the approximate range of 0.6:1 to 3:1.

12. The method of claim 11 wherein the amounts of said 3-amino-L-tyrosine and said 5-amino-2,3-dihydro-1,4-phthalazinedione are approximately equimolar.

* * * * *

UNITED STATES PATENT AND TRADEMARK OFFICE
CERTIFICATE OF CORRECTION

PATENT NO. : 5,003,050
DATED : March 26, 1991
INVENTOR(S) : Johnathan L. Kiel et al It is certified that error appears in the above-identified patent and that said Letters Patent is hereby corrected as shown below:

Column 6, line 60, after "sodium nitrite at", insert -- 20 mM. --.

Signed and Sealed this

Second Day of February, 1993

Attest:

STEPHEN G. KUNIN

Attesting Officer      Acting Commissioner of Patents and Trademarks